(12) United States Patent
Drzal et al.

(10) Patent No.: US 6,723,802 B2
(45) Date of Patent: Apr. 20, 2004

(54) EPOXY RESIN AND POLYGLYCOSIDE BASED POLYMERS AND PROCESS FOR THE PREPARATION THEREOF

(75) Inventors: Lawrence T. Drzal, Okemos, MI (US); Seong Ok Han, Kyungki-do (KR)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 10/223,266

(22) Filed: Aug. 19, 2002

(65) Prior Publication Data

US 2003/0109603 A1 Jun. 12, 2003

Related U.S. Application Data

(60) Provisional application No. 60/314,879, filed on Aug. 24, 2001.

(51) Int. Cl.[7] .............................. C08K 3/04; C08K 3/36; C08K 7/02; C08L 5/00; C08L 63/02
(52) U.S. Cl. ...................... 525/532; 523/446; 523/466; 523/468
(58) Field of Search ................................ 523/446, 466, 523/468; 525/530, 532, 533

(56) References Cited

U.S. PATENT DOCUMENTS 3,870,664 A * 3/1975 Faulkner
5,872,199 A * 2/1999 Bloembergen et al. .. 526/238.2
6,242,593 B1 * 6/2001 Bloembergen et al. .. 536/123.1

OTHER PUBLICATIONS

Chemical abstracts accession No. 1981:499355, Litter et al., "Synthesis of alkyd resins from sucrose and vegetable oils," Acta Cientifica Venezolana, vol. 31, No. 5 (1980), pp. 398–403.*

Chemical abstracts accession No. 1967:4116987, Gamova et al., "Determination of the molecular weight of wood sugars," Gidroliznaya i Lesokhimicheskaya Promyshlennost, vol. 20, No. 2 (1967), p. 15.*

* cited by examiner

Primary Examiner—Robert Sellers
(74) Attorney, Agent, or Firm—Ian C. McLeod

(57) ABSTRACT

Epoxy resin polyglycoside-based cured polymers and process for the preparation are described. A particular epoxy resin precursor is the diglycidyl ether of bisphenol A. A particular glucose based polymer is a glucose malic acid ester-vinyl copolymer. The polymers have a degree of biodegradability because of the polyglycoside as well as elevated temperature stability and are useful in transportation vehicle settings. Natural source fillers, such as cellulose fibers, which are treated or untreated, exfoliated clays or exfoliated graphite can be used.

22 Claims, 8 Drawing Sheets

Cellulose Nanowhiskers as Reinforcements for Polymer Composites

- Cellulose microfibrils
  - (5nm x 150-300nm)
  - monocrystalline cellulose domains parallel to the microfibril axis composed of cellulose chains in a cellulose lattice bonded laterally and surrounded by surface chains forming a paracrystalline envelope
  - devoid of defects, linked by amorphous domains having a strength of 10 GPa
  - tensile modulus of 130 GPa
  - reinforcement for polymers

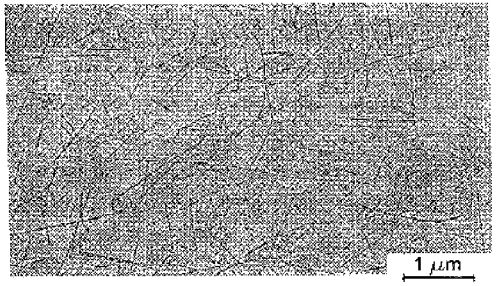

*TEM micrograph of cellulose whiskers from tunicate (Favier, et. al)*

FIG. 13

EPOXY RESIN AND POLYGLYCOSIDE BASED POLYMERS AND PROCESS FOR THE PREPARATION THEREOF

CROSS REFERENCE TO RELATED APPLICATION

This application is based for priority upon provisional application Serial No. 60/314,879, filed Aug. 24, 2001.

BACKGROUND OF THE INVENTION

(1) Field of the Invention

The present invention relates to cured epoxy resin and polyglycoside-based cured polymers and to a process and compositions for the preparation of these polymers. In particular, the present invention relates to the curing of epoxy resin precursors with a polyglycoside based polymer. The polymers can contain fillers of various known types, preferably those which are natural. The polyglycoside moiety provides a degree of biogradability to the resulting polymer not usually available in epoxy resin based polymers. The polymers are stable to elevated temperatures up to 300° C., and thus are useful in vehicle engine compartments for sound deadening and the like.

(2) Description of Related Art

Recently, there has been increasing interest in the use of biocomposites of natural fibers, particularly cellulosic fibers, especially in the automobile industry. These composites are reported to offer advantages of ~20% reduction in processing temperature and ~25% reduction in cycle time in addition to a weight reduction of about ~30% over conventional glass fiber composites (Saheb, D. N., et al., Advances in Polymer Technology 18 4 351 (1999)). For automotive applications biocomposites have to meet several demanding requirements such as temperature resistance and wet environmental resistance (Reussmann, T., et al., Advanced Engineering Materials 1, 2, 140 (1999)). The incorporation of biobased polymer with natural fibers would be the best combination for development of environmentally friendly composites if the developed biocomposites meet the demanding requirements.

Glucose maleic acid ester vinyl copolymer (GMAEVC) has been developed to use as a biodegradable adhesive for the paper and packaging industry. GMAEVC contains reactive carboxylic and hydroxyl functional groups in its structure. This leads to cost effective and better performing of biocomposites.

U.S. Pat. Nos. 5,869,173 and 6,171,688 to Zheng to al show composites which can be formed.

OBJECTS

It is therefore an object of the present invention to provide novel epoxy resin and polyglycoside based polymers. Further, it is an object of the present invention to provide such polymers which have a degree of biodegradability and high temperature resistance. These and other objects will become increasingly apparent by reference to the following description and the Figures.

SUMMARY OF THE INVENTION

The present invention relates to a curable polymer composition which comprises:

(a) an epoxy resin precursor; and
(b) a co-polymer of a polyglycoside acid or acid ester reacted with an organic anhydride or acid, and optionally with a vinyl monomer, wherein the ratio of (a) to (b) produces a cured polymer composition.

In particular the present invention relates to a curable polymer composition which comprises:

(a) an epoxy resin precursor; and
(b) a copolymer of a polyglycoside acid or acid ester of the formula II or III as follows:

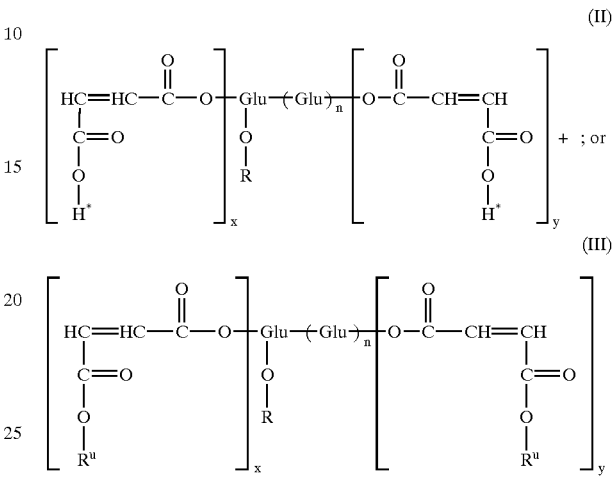

and mixtures thereof and optionally a vinyl monomer, wherein R and R" are alkyl containing 1 to 30 carbon atoms and wherein the ratio of (a) to (b) produces a cured polymer composition. X and y are integers between 0 and 4 but x and y are not O at the same time.

The present invention particularly relates to a curable polymer composition which comprises:

(a) liquid epoxy resin; and
(b) a copolymer of the formula as follows:

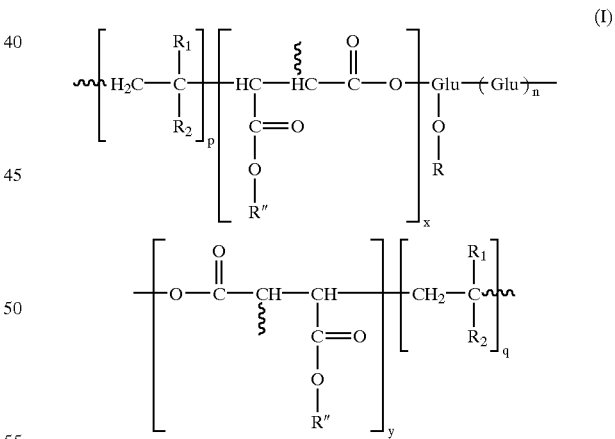

wherein Glu is a saccharide moiety which is derived from a sugar selected from the group consisting of α-D-glucose, fructose, mannose, galactose, talose, gulose, allose, altrose, idose, arabinose, xylose, lyxosc, ribose, and mixtures thereof, or by hydrolysis of a material selected from the group consisting of starch, corn syrups, maltodextrins, maltose, sucrose, lactose, maltotriose, xylobiose, mellibiose, cellobiose, raffinose, stachiose, levoglucosan, 1,6-anhydroglucofuranose, and mixtures thereof, and wherein the ratio of (a) to (b) produces a cured polymer composition, wherein $R_1$ and $R_2$ are substituent groups of a vinyl monomer or mixture of vinyl monomers, wherein said vinyl monomer or mixture of vinyl monomers is selected from the group consisting of vinyl acetate, ethyl hexyl acrylate, butyl acrylate, ethyl acrylate, hydroxyethyl acrylate, hydroxyethyl methacrylate, lauryl acrylate, methyl methacrylate, methacryclic acid, acrylic acid, other acrylates, mixtures of different acrylate monomers, ethylene, 1,3-butadiene, styrene, vinyl chloride, vinylpyrrolidinone, other vinyl monomers, and mixtures thereof, R is selected from the group consisting of a C1 to C30 alkyl and mixtures thereof, R" is selected from the group consisting of a C1 to C30 alkyl and mixtures thereof, or a hydrogen, n is an integer ranging from 0 to 10; x and y are integers ranging from 0 to 4, but not x and y are 0 at the same time, p and q are integers ranging from 0 to 1000, but not both p and q are zero, and wherein ~~~ indicates continuing polymer chains.

Preferably Glu is an α-D-glucose moiety. Preferably the molar ratio of (a) to (b) is about 1:1. Preferably an alkyl polyglycoside is reacted with malic anhydride to form the polymer which is reacted with the vinyl monomer to form the copolymer. Preferably $R^1$ and $R^2$ and R" are selected from the group consisting of hydrogen and n-butyl.

The composition includes a filler. A fiber, particularly a cellulosic fiber, is preferred. Clay can be used as a filler. The compositions are cured to solid resins with or without the fillers.

The present invention also relates to a process for forming a cured polymer composition which comprises:

(a) providing a mixture of (1) a liquid mixture of an epoxy resin precursor and (2) a polyglucoside-organic anhydride reaction product which has optionally been polymerized with a vinyl monomer, wherein the ratio of (1) to (2) provides the cured polymer composition; and (b) heating the mixture to produce the cured polymer.

In particular the present invention relates to a process for forming a cured polymer composition which comprises:

(a) providing (1) a liquid epoxy resin precursor and (2) a liquid copolymer of a polyglycoside acid or acid ester of the formula II or II as follows:

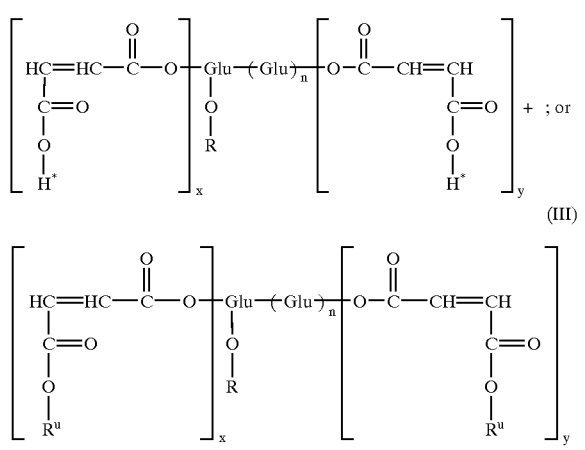

and mixtures thereof which has optionally been reacted with a vinyl monomer wherein R and $R^{11}$ are alkyl contain 1 to 30 carbon atoms, x and y are integers between 0 and 4 but not x and y are o at the same time and wherein the ratio of (1) to (2) produces the cured polymer composition; and (b) heating the mixture to produce the cured polymer composition.

Further, the present invention relates to a process for the preparation of a cured polymer composition which comprises:

(a) providing a mixture of
(1) a liquid epoxy resin; and
(2) a liquid copolymer of the formula I as follows:

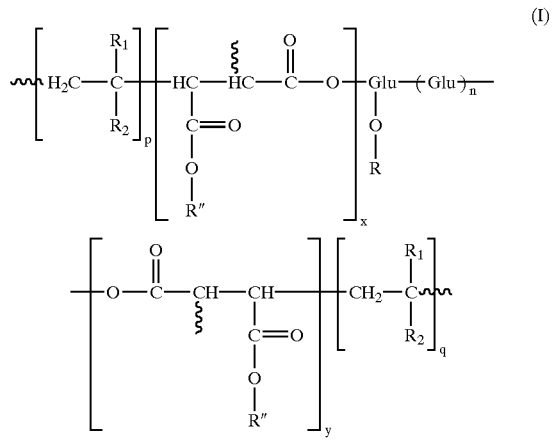

wherein Glu is a saccharide moiety which is derived from a sugar from the group consisting of α-D-glucose, fructose, mannose, galactose, talose, gulose, allose, altrose, idose, arabinose, xylose, lyxosc, ribose, and mixtures thereof, or by hydrolysis of a material selected from the group consisting of starch, corn syrups, maltodextrins, maltose, sucrose, lactose, maltotriose, xylobiose, mellibiose, cellobiose, raffinose, stachiose, levoglucosan, 1,6-anhydroglucofuranose, and mixtures thereof, wherein $R_1$ and $R_2$ are substituent groups of a vinyl monomer or mixture of vinyl monomers, wherein said vinyl monomer or mixture of vinyl monomers is selected from the group consisting of vinyl acetate, ethyl hexyl acrylate, butyl acrylate, ethyl acrylate, hydroxyethyl acrylate, hydroxyethyl methacrylate, lauryl acrylate, methyl methacrylate, methacryclic acid, acrylic acid, other acrylates, mixtures of different acrylate monomers, ethylene, 1,3-butadiene, styrene, vinyl chloride, vinylpyrrolidinone other vinyl monomers, and mixtures thereof, R is selected from the group consisting of a C1 to C30 alkyl and mixtures thereof, R" is selected from the group consisting of a C1 to C30 alkyl and mixtures thereof, or a hydrogen, n is an integer ranging from 0 to 10; x and y are integers ranging from 0 to 4, but not x and y are 0 at the same time, p and q are integers ranging from 0 to 1000, but not both p and q are zero, and wherein ~~~ indcates continuing polymer chains, and wherein the ratio of (1) to (2) produces a cured polymer composition; and (b) heating the mixture to produce the cured polymer composition.

Preferably $R^1$, $R^2$ and R" are selected from the group consisting of hydrogen and n-butyl. The epoxy resin precursor is preferably derived from the diglycidyl ether of bisphenol A. Preferably the epoxy resin precursor is derived from the diglycidyl ether of bisphenol A.

A "Glycoside" is a compound of a sugar with another substance, wherein sugar hydrolyzes to its constituents: glucosides yield glucose, fructosides yield fructose, galactosides yield galactose, and the like.

A "polyglycoside" is a polymerized glycoside wherein multiple sugars are joined together and then connected to another organic group.

The present invention particularly relates to an environmentally friendly biocomposites polymer matrix composed of glucose based copolymer and epoxy resin and to biocomposites with natural fibers, particularly cellulosic fibers, as reinforcements. The primary advantage of this invention over previous approaches are that the polyglycoside polymers are environmentally friendly and cost effective. The polymer matrix for this invention is preferably composed of 50 wt % by weight of glucose based copolymer and 50% by weight of epoxy resin. The glucose based copolymer is a biodegradable. The preferred glucose based copolymer is thus used as a hardener for epoxy resin of the polymer matrix formulation. Hence the polymer matrix formulations do not need any toxic and expensive curing agents that are used to conventional epoxy curing systems.

The cured polymer matrix shows the relatively constant performances in the wide ranges of curing conditions. The curing process of the polymer matrix depends only on the energy that induces the reaction between glucose based copolymer and epoxy resin. Hence a temperature controlled convection oven can be necessary for the even temperature distributions on curing of the samples for the scale up. The poor heat transfer property of the polymer matrix can cause the sticky property of the less cured polymer matrix or volume shrinkage of the over cured polymer matrix if the curing is not controlled. The lamination of the polymer matrix sheets to fillers can be alternative methods for implementation. Alternatively microwave, RE electron beam and UV processing can be used.

The matrix formulation is very stable at room temperature so the pot life is long enough for applying it to the fabrication process. The cured polymer matrix shows thermal stability up to 300° C. and maintains the mechanical performance in wet environments. The polymer shows good compatibility with hydrophilic natural fibers, particularly cellulosic fibers, to fabricate biocomposites, making special treatments of hydrophobic polymer matrix or hydrophilic fiber surface to improve the adhesion unnecessary. The markets for this invention can be expected for the transportation, infrastructure and building industries.

The fillers and their properties are shown in Table 1.

BRIEF DESCRIPTION OF FIGURES

FIGS. 11 to 13 show various cellulosic fibers.

DESCRIPTION OF PREFERRED EMBODIMENTS

The preferred polyglycoside based polymers are described in U.S. Pat. Nos. 5,872,199 and 6,242,593 to Bloembergen et al which are incorporated "herein in their entirety." With by reference. The reaction of a $C_1$ to $C_{30}$ alkyl polyglycoside with an organic anhydride yields the polyglycoside acid or acid ester co-polymer.

The epoxy resins are well known to those skilled in the art and are described in Kirk-Othmer, John Wiley & Sons, 9 267–290 (1980). They are available from a variety of commercial sources including Shell Co., Ciba, and The Dow Chemical Company.

TABLE 1

Comparative properties of some natural fibers with conventional man-made fibers

| FIBER | DENSITY (G/CM$^3$) | DIAMETER ($\mu$M) | TENSILE STRENGTH (MPA) | YOUNG'S MODULUS (MPA) | ELONGATION AT BREAK (%) |
|---|---|---|---|---|---|
| Cotton | 1.5–1.6 | — | 287–800 | 5.5–12.6 | 7.0–8.0 |
| Jute | 1.3–1.45 | 25–200 | 393–773 | 13–26.5 | 1.16–1.5 |
| Flax | 1.50 | — | 345–1100 | 27.6 | 2.7–3.2 |
| Hemp | — | — | 690 | — | 1.6 |
| Ramie | 1.50 | — | 400–938 | 61.4–128 | 1.2–3.8 |
| Sisal | 1.45 | 50–200 | 468–640 | 9.4–22.0 | 3–7 |
| PALF | — | 20–80 | 413–1627 | 34.5–82.51 | 1.6 |
| Coir | 1.15 | 100–450 | 131–175 | 4–6 | 15–40 |
| E-glass | 2.5 | — | 2000–3500 | 70 | 2.5 |
| S-glass | 2.5 | — | 4570 | 86 | 2.8 |
| Aramid | 1.4 | — | 3000–3150 | 63.67 | 3.3–3.7 |
| Carbon | 1.7 | — | 4000 | 230–240 | 1.4–1.8 |

Figure 11:
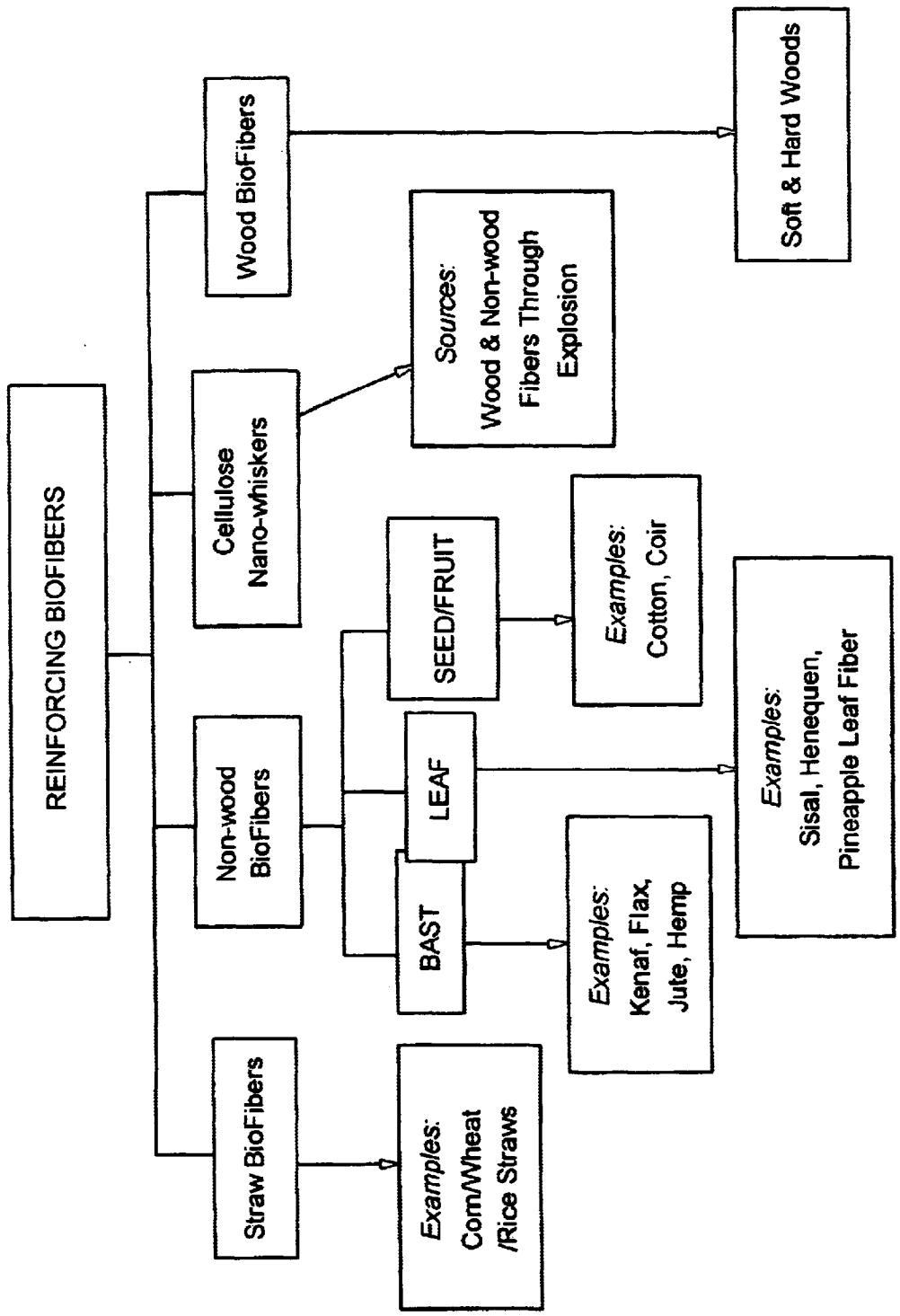
Figure 12:
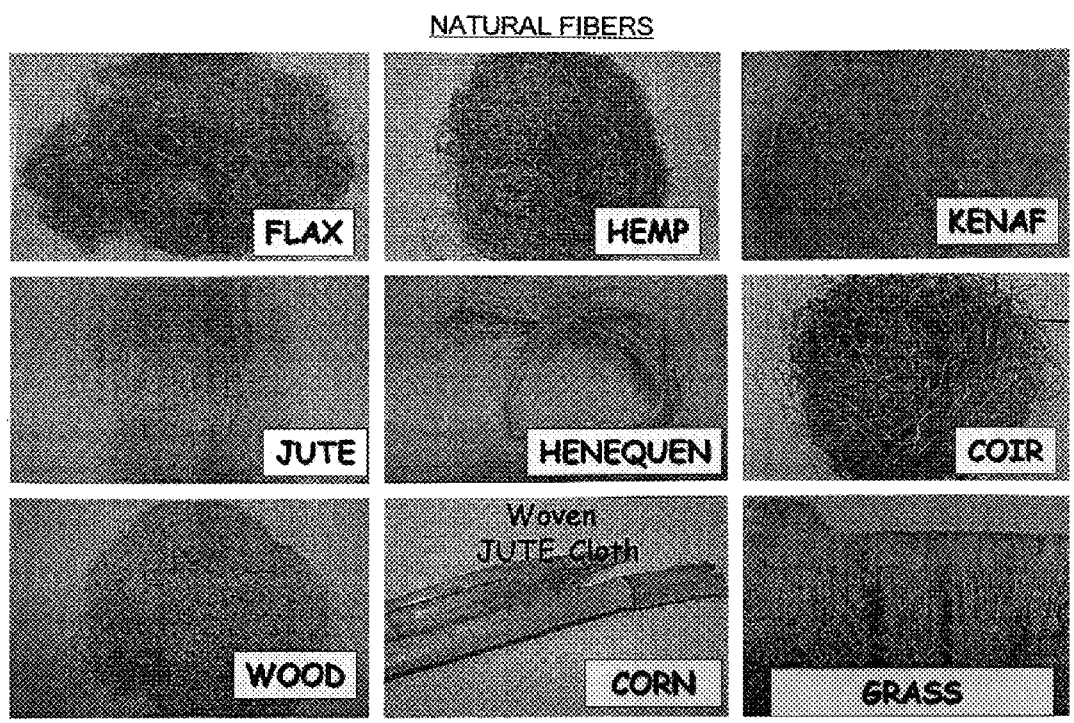

The cellulosic fibers are preferred, particularly cellulosic nanofibers (See FIGS. 11 to 13). Exfoliated clays and graphites can also be used as fillers.

Bisphenol A type EPON-828 (Shell Co.), is an epoxy resin precursor with the bisphenol A structure and a molecular weight of 380, and has the formula:

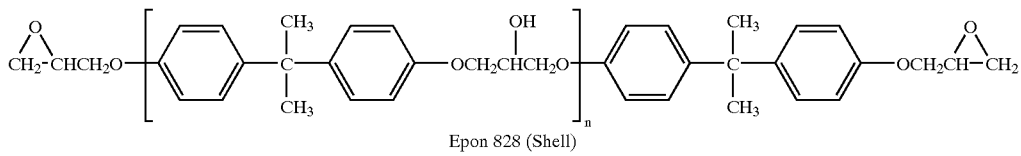
Epon 828 (Shell)

wherein n=0 (88%); n=1 (10%); n=2 (2%).

Bisphenol-A type, DER 331 (Dow Chemical Co., Midland, Mich.), is an epoxy polymer precursor and is an analog to Epon-828 having the formula:

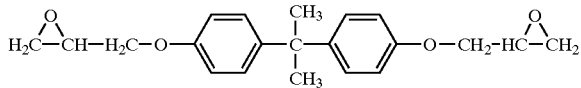

Bisphenol-F type, DER 354 (Dow Chemical Co.) is an epoxy polymer precursor having the formula:

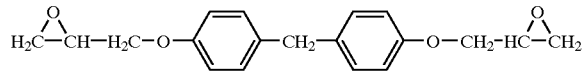

Novolac type, DER 43, DER 438 and DER 439 (Dow Chemical Co.) are epoxy polymer precursors having the formula:

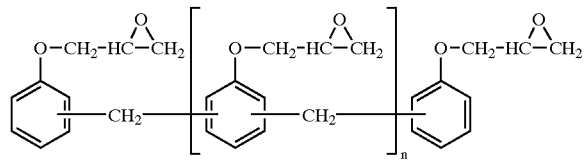

wherein n is between about 0.2 and 1.8.

Epoxy polymer, DER 732 (Dow chemical Co. is an epoxy resin precursor of the general formula:

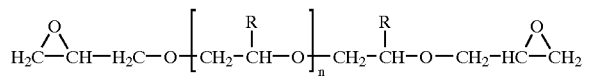

There are numerous other types of epoxy polymer precursors which are suitable and which are well known to those skilled in the art.

Amine curing agents can be used to cure the epoxy resin precursors into a solid epoxy resin along with the polyglycoside-based polymer, although this is not preferred. Curing agents are, for instance, linear polyoxypropylene di- or triamines which are sold as JEFFAMINES, Huntsman Chemical Company, Austin, Tex. The polyoxypropylene diamines (D-series) of the formula:

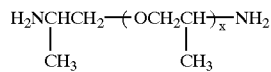

wherein x is between about 4 and 40 can be used.

The linear diamines previously described when used as curing agents for the epoxy resin precursors produce a glass transition temperature of less than ambient temperatures (25° C.) And preferably less than 0° C. As a result, when cured to a pristine epoxy resin without any filler, the resins are flexible when x is between about 4 and 40 in the polyoxypropylene diamine, the cured epoxy resin is also elastic.

The T series JEFFAMINES can be used. These are

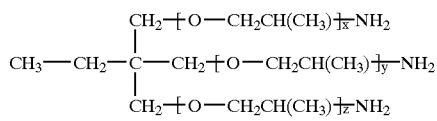

wherein x+y+z between about 4 and 120.

Various other epoxy resin curing agents, such as anhydrides and amides, can be used. The amide curing agents are for instance

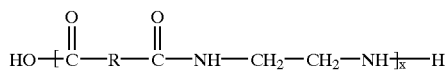

where X is between about 5 and 15.

EXAMPLES

A blend of DGEBA based epoxy resin and glucose maleic acid ester vinyl copolymer (GMAEVC) as a matrix for composites was used in order to develop environmentally friendly biocomposites for high temperature automotive applications. The reaction mechanism of DGEBA and GMAEVC was investigated by DSC and FTIR methods. Three different exothermic reactions were identified upon curing and attributed to etherification and esterification reactions of the hydroxyl and carboxylic functionalities of GMAEVC with the epoxy groups of the DGEBA resin. The cured matrix containing 50 wt % of GMAEVC showed thermal stability up to 300° C. The glass transition temperature and storage modulus of the matrix were as high as 97° C. and 2700 Pa, respectively. A water absorption test was performed to examine the stability of this matrix in wet environments. A slight weight increase and glass temperature decrease of the matrix due to water uptake were observed. However, the matrix did not show any change in mechanical performance and the original glass transition temperature was recovered after heating the matrix up to 150° C. Biocomposites composed of this matrix and henequen fibers with different conditions were manufactured and characterized. This formulated matrix showed good compatibility with henequen fibers. Finally, this study illustrates the possible future developments of biocomposites for high temperature automotive applications based on a blend of DGEBA and GMAEVC as a matrix and natural fibers as reinforcements.

Epoxy resin Epoxy resin, Tactix 123, based on diglycidyl ether of bisphenol A (DGEBA) was purchased from Ciba Chemical Co. The viscosity of the resin is 5000 cps at 25°

C. and the epoxy equivalent weight is 172–176 g/mol. The structure of the monomer is shown in Structure 1.

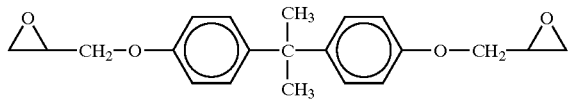

Structure 1: The DGEBA Molecule

Glucose maleic acid ester vinyl copolymer GMAEVC was obtained from EcoSynthetix Co. (Lansing, Mich.) and used as received. The average molecular weight of GMAEVC is 420 g/mol. The structure of GMAEVC is shown in Structure 2. Degrees of polymerization of glucose (x) and of substitution of maleate ester group (y) are 1.1–1.3 and 1.4, respectively. The substituents of GMAEVC ($R'''$, $R^1$, $R^2$) are either hydrogen or n-butyl groups (U.S. Pat. No. 5,872,199 (1999), B. Steven). GMAEVC starts to decompose at 165° C. and degrades at temperatures over 110° C. The comparison of FTIR spectra between original GMAEVC and the degraded GMAEVC shows that the —C—O—C— peak characteristic of the glucose and vinyl groups peaks disappeared. A new peak due to the presence of free —C(O)—O$^-$ functional group appeared with the GMAEVC degradation. It was also found that the broad peak for the hydroxyl group changed to a sharp peak when the glucose ring opened and formed free hydroxyl groups (S. O. Han, 222nd *American Chemical Society Meeting; Polymer Priprint*, (2001)).

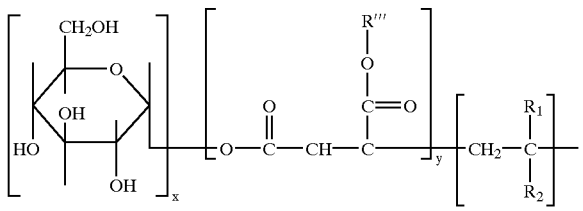

Structure 2: Glucose Maleic Acid Ester Vinyl Copolymer Molecule

Henequen fiber Henequen (*Agave fourcroydes*) fibers were obtained from Cordemex, S. A. of Merida, Yucatan, Mexico. Henequen fibers were washed with water and dried in air. Dried henequen fibers were vacuum dried at 110° C. for one hour and used as raw henequen fibers. Raw henequen fibers were treated in NaOH solutions of different concentrations to prepare alkali treated henequen fibers. Raw henequen fiber was immersed in 2,5,10 wt % NaOH solutions for one hour, respectively, then washed with running water. The fibers were neutralized with 2 wt % acetic acid solution, washed with water and dried in air. Alkali treated henequen fibers were vacuum dried for one hour prior to composite fabrication. The properties and surface composition of raw and alkali treated henequen fibers were compared with TGA and XPS analysis.

Experimentation The blend of 50 wt % of DGEBA and GMAEVC was chosen to investigate the curing reaction between DGEBA and GMAEVC and the performance of the cured matrix.

DSC monitoring of the reaction between DGEBA and GMAEVC A DSC study was performed under a nitrogen atmosphere using a DSC2920 modulated differential scanning calorimeter from TA instruments. High purity indium was used to calibrate the calorimeter. Real time monitoring of the curing of DGEBA and GMAEVC was performed in an aluminum pan in the 30° C. to 350° C. temperature ranges.

FT-IR monitoring of th reaction between DGEBA and GMAEVC Curing of DGEBA with GMAEVC was quantitatively analyzed by transmission FTIR spectroscopy using a Perkin Elmer FTIR system 2000 model, equipped with a conventional TGS detector. Samples were prepared by casting a thin film of resin onto a sodium chloride plate and placed in a heating cell in the spectrometer to carry out the reaction from 100° C. to 180° C. at a heating rate of 1° C./min. The temperature of the heated cell was monitored with a DigiSense temperature controller from the Cole Parmer Co. The FTIR spectra were collected at different temperatures and compared to the FTIR spectra of fully cured samples prepared in an oven to confirm the polymerization products. The conversion of epoxy and hydroxyl groups in the formulation based on DGEBA and GMAEVC were calculated from the FTIR spectra. The 1509 cm$^{-1}$ band was unchanged upon curing, and subsequently, was used as an internal standard (B. Defoort, *SAMPE International Symposium*, (2001)). The decrease of the band at 912 cm$^{-1}$ assigned to the epoxy function permits accurate measurement of the monomer conversion via the following relation, where Π is the functional conversion and T is temperature. For the hydroxyl function conversion the maximum point of the hydroxyl group peak in the region of 3650–3124 cm$^{-1}$ was measured at each temperature.

$$\Pi(epoxy) = 1 - \frac{\frac{A_{912(T)}}{A_{1509(T)}}}{\frac{A_{912(T=100)}}{A_{1509(T=100)}}} \quad \Pi(hydroxyl) = 1 - \frac{\frac{A_{max(T)}}{A_{1509(T)}}}{\frac{A_{3512(T=100)}}{A_{1509(T=100)}}}$$

Thermo-mechanical Analysis The glass transition temperature and the modulus of the cured DGEBA and GMAEVC were measured by dynamic mechanical analysis in the single cantilever mode, at a frequency of 1 Hz. DMA runs were recorded with a DMA 2980 Dynamic Mechanical Analyzer from TA instruments. The glass transition temperature was measured at the maximum of the Tan delta (δ) curve deduced from DMA experiments. Storage modulus of the matrix was determined at 40° C.

Thermal stability Analysis Thermal stability of the cured matrix was analyzed under a nitrogen atmosphere using a TGA2950 thermal gravimetric analyzer from TA instruments. The thermal stability of raw and alkali treated henequen fibers were also evaluated.

Surface Analysis X-ray Photoelectron Spectroscopy examination was used to determine the functional groups on the surface of the cured matrix. Perkin Elmer Physical Electronics PHI 5400 ESCA Spectrometer equipped with standard magnesium X-Ray source operated at 300 W (15 kV and 20 mA) was used for surface analysis. Surface analysis of raw henequen and alkali treated henequen fibers were also measure and compared.

Procedure

Matrix Preparation DGEBA and GMAEVC were heated to 90° C. separately and mixed by a melt-blending process. This mixture was used to study the curing of DGEBA and GMAEVC by DSC and FTIR in real time. The mixture was degassed for 10 minutes in a vacuum oven at 90° C. and cured in a silicone mold (1.2 cm×7.5 cm×0.03 cm). Curing was completed with heating the matrix at 175° C. for 2 hours and 200° C. for 2 hours, consecutively, in an air-circulating oven at a heating rate of 5° C./min.

Water Absorption Test on Matrix To investigate the stability of the cured matrix of DGEBA and GMAEVC in wet conditions the water absorption test was performed. The cured matrices were dried in an oven at 110° C. for one hour. Immediately upon cooling, the specimens were weighed. The specimens were immersed in distilled water at ambient temperature and weighed at predetermined times. Every procedure was performed by following ASTM D570-98: Standard test methods for water absorption of plastics (ASTM D570-98; Standard test methods for water absorption of plastics). The specimen size was 1.2 cm×7.5 cm×0.03 cm and the water gain percentage, M %, was determined from the equation:

$$M\% = \frac{(W - W_d)}{W_d} \times 100$$

W is the weight of the water absorbed specimen and $W_d$ is the initial weight of the dry specimen. To ensure the removal of excessive surface water, specimens were gently wiped dry using clean, lint-free tissue paper and allowed to stand free at ambient environment for 2 minutes. To examine the reaction between water and the matrix, the specimen that was immersed in the water for 1056 hours was dried in an air-circulating oven at 110° C. for an hour. The weight gain of this specimen was compared to the weights of both dried and water absorbed for 1056 hours specimen.

Preparation of Biocomposites with the Matrix and

Henequen fibers Henequen fibers were vacuum dried for one hour prior to composite fabrication. The degassed matrix was poured onto the henequen fibers in silicone molds and degassed. The composite was cured at 175° C. for 2 hour and 200° C. for 2 hours, consecutively, at a heating rate of 5° C./min. The fiber loading was determined by the fibers weight and fiber density. The density of henequen fiber was determined as 0.44 g/cm$^3$ by the density measurement. The calculated amount of henequen fiber in the matrix was approximately 40 vol %.

Results and Discussion

Matrix Characterization Characterization of the matrix was performed to examine the possibility of utilizing this matrix for biocomposite applications with henequen fibers.

Figure 1:
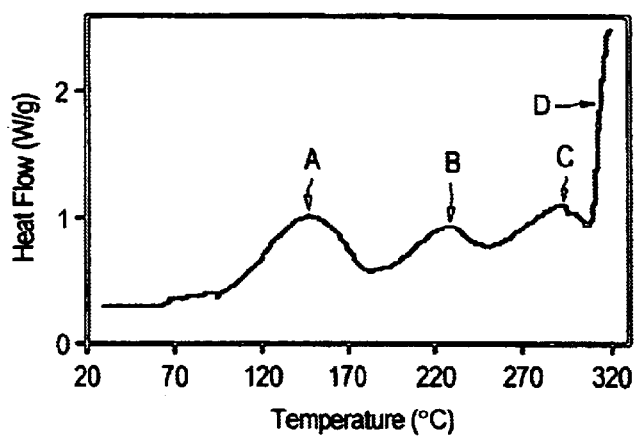
FIG. 1 is a graph of a DSC Scan of DGEBA and GMAEVC Blend.

DSC monitoring of the reaction A DSC scan of a mixture of DGEBA and GMAEVC during heating from 30° C. to 350° C. is shown in FIG. 1. Three exothermal peaks are observed in the regions of 90–170° C., 180–240° C. and 260–300° C., respectively. These peaks are attributed to the hydroxy-epoxy etherification, carboxylic-hydroxyl esterification and carboxylic-epoxy esterification. The highest peak (D) could be attributed to the decomposition of the DGEBA (S. O. Han, 222nd *American Chemical Society Meeting; Polymer Priprint*, (2001)).

Figure 2:
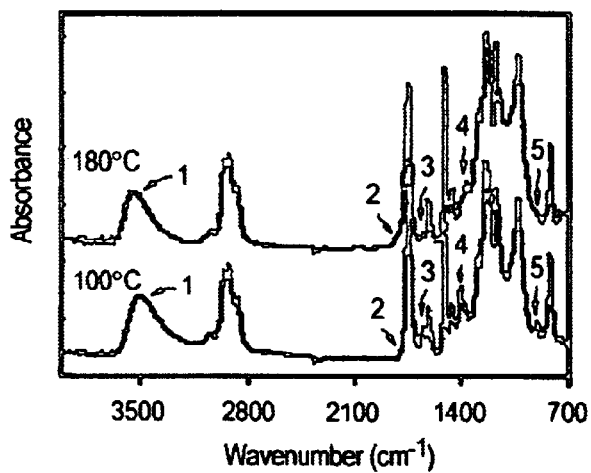
FIG. 2 is a graph of a FTIR spectra of DGEBA and GMAEVC blend.

FT-IR monitoring of the reaction between DGEBA and GMAEVC Curing of DGEBA and GMAEVC was monitored in real-time during heating from 100° C. to 180° C. and FTIR spectra obtained at 100° C. and 180° C. are compared in FIG. 2. The peak due to hydroxyl groups (180° C.-1) is shifted toward higher frequency resulting from the ester or ether bond formation near hydroxyl groups. The epoxy peak (100° C.-5) and the vinyl group peaks (100° C.-3, 100° C.-4) disappeared as curing of DGEBA and GMAEVC and degradation of GMAEVC proceeded. A new peak appeared at 1795 cm$^{-1}$ (180° C.-2) upon heating above 175° C. This peak was also observed in the samples cured at temperatures higher than 175° C. The intensity of the peak increased with increasing curing temperature (G. Socrates, *Infrared Characteristic Group Frequencies*, pp.45–47, 57–73, (1980)).

Figure 3:
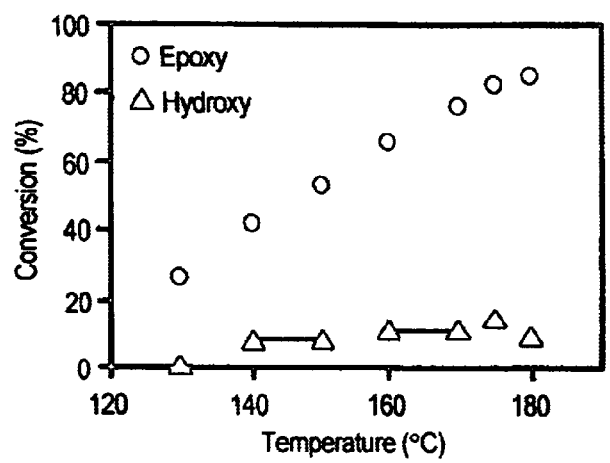
FIG. 3 is a graph of a conversion of epoxy and hydroxyl groups of DGEBA and GMAEVC blend.

FIG. 3 shows the epoxy and hydroxyl groups conversions of DGEBA and GMAEVC blend when the blend is heated from 100° C. to 180° C. Epoxy group conversion increases continuously when the temperature increases, but the hydroxyl group conversion starts to increase around 130–150° C. and shows a very slow increase with increasing temperature. The curing reaction between epoxy groups of DGEBA and carboxyl and hydroxyl groups of GMAEVC can be considered as etherification and esterification reactions (H. Lee, *Handbook of Epoxy Resin*, pp.5:16–5:20, (1982)).

Figure 4:
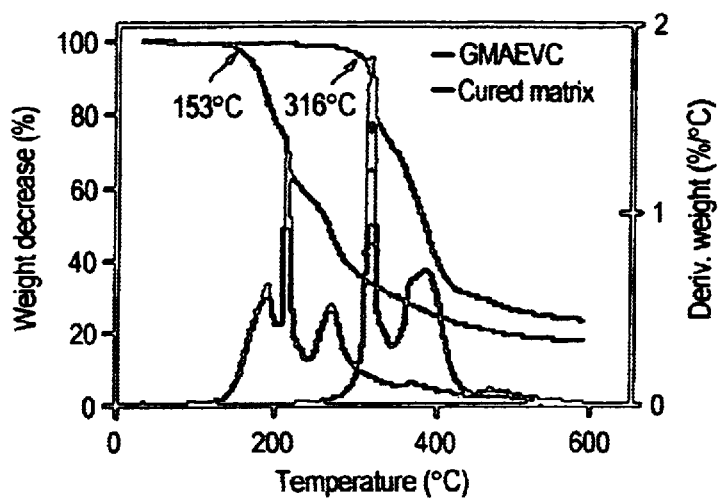
FIG. 4 is a graph showing a TGA curves of GMAEVC and cured matrix.

Thermal Stability and Mechanical Performance of Cured Matrix of DGEBA and GMAEVC FIG. 4 shows the comparison of the thermal stability of GMAEVC alone and the cured matrix of DGEBA and GMAEVC. The cured matrix shows thermal stability up to 300° C. and three products decomposed between 300–400° C. The glass transition temperature and the storage modulus of the cured matrix of DGEBA and GMAEVC are as high as 97° C. and 2700 Pa, respectively. The GMAEVC alone starts to decompose at 140° C. and three products decompose in the 150–300° C.

Figure 5A:
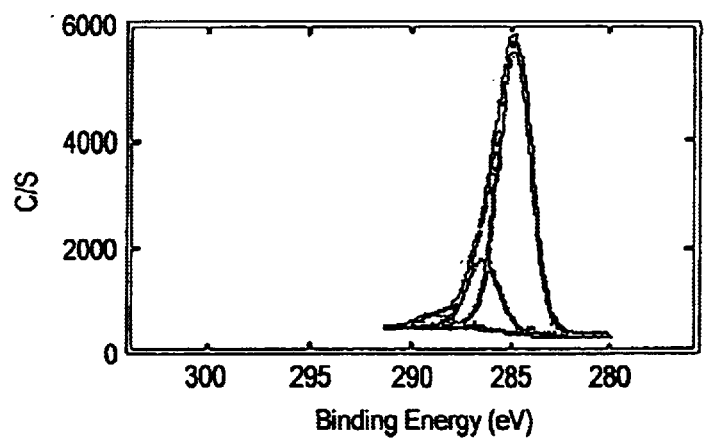
FIGS. 5A and 5B are graphs of C1s and O1s spectra of the cured matrix of DGEBA and GMAEVC.
Figure 5B:
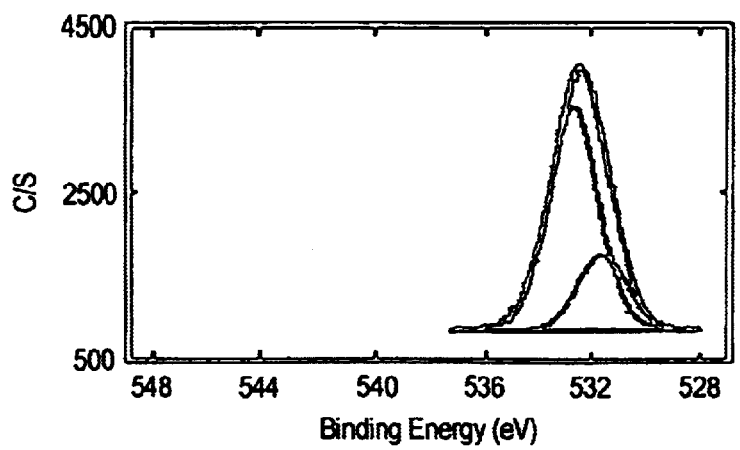

Surface analysis of cured matrix of DGEBA and GMAEVC Surface analysis of the cured matrix is shown in Table 1. FIGS. 5A and 5B show the C1s and O1s deconvoluted spectra with the binding energy. The carbon 1s spectrum is deconvoluted to three peaks at 284.6, 286.1 and 287.6 eV, respectively. The peaks are assigned to carbon bind with another carbon or hydrogen (—C—C*—C—, —C*—H), carbon bind with one oxygen atom (—C*—O—H, —C*—O—C—) and carbon bind with two oxygens (—O—C*—O—, —C(O)—O—), respectively. The oxygen is spectra is deconvoluted to two peaks at 530.0 and 532.0 eV that are assigned —O—C—O*— and —C—O*H. These hydrophilic groups on the surface of the cured matrix can be bound to water available from the surroundings. Silicone atom is considered to come from the silicone mold.

TABLE 2

Atomic Ratio of the Cured Matrix Blend

| | [C] % | [O] % | [O]/[C] | [Si] % |
|---|---|---|---|---|
| Cured Matrix | 78.4 | 18.7 | 0.24 | 3.0 |

Water Absorption Test on the Cured Matrix Blend The cured matrix contains hydrophilic functionalities and can absorb moisture. The absorbed water can lead to dimensional variations in composites and also affect the mechanical properties of the composites. Water absorption tests on this matrix were performed and the performance of samples was compared to the dry, original samples.

Figure 6:
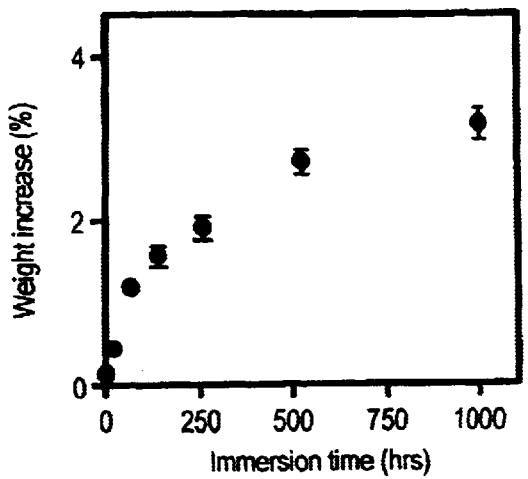
FIG. 6 is a graph showing water absorption of the cured matrix of DGEBA and GMAEVC versus time.

Water Absorption Profile of Cured Matrix The weight increase of the cured matrix due to water uptake is plotted in FIG. 6 versus time. The weight of the matrix increased by 3.2% after 1056 hours of immersion in water. When the sample is heated at 110° C. in an oven for one hour, the weight gain decreases to 1.9%.

Figure 7A:
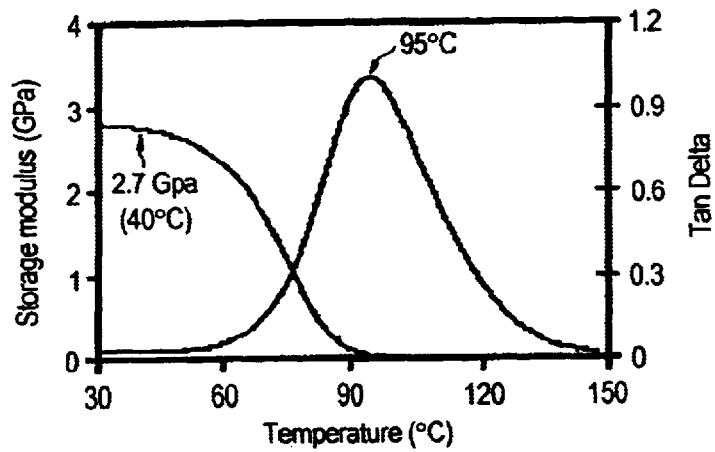
FIGS. 7A and 7B are graphs showing performance changes of the cured matrix after water absorption test.
Figure 7B:
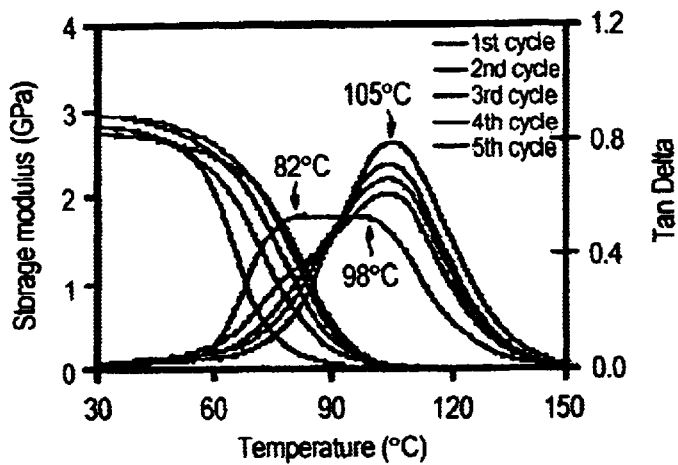

Effects of Water Absorption on Mechanical Performances of the cured matrix Storage modulus and Tan delta (δ) of the cured matrix before and after water absorption are compared in FIGS. 7A and 7B. The maximum peak of Tan (δ) that is related to the glass transition temperature is changed to a convoluted peak for the matrix that immersed in water for 1056 hours. The convoluted peak is changed to the single peak that is the same of the original cured matrix when the water uptake specimen is conditioned using the DMA cycling test. Heating the specimen up to 150° C. and cooling it down to room temperature is one DMA cycle. The glass transition temperature of the cured matrix is changed from 95° C. for the original matrix to 82° C. and 98° C. for the matrix that was immersed in water for 1056 hours. This glass transition temperature shows a constant value as 150° C. after the second DMA cycle. Because the cured matrix of DGEBA and GMAEVC has hydrophilic functional groups on the surface, water can be bound to the surface of the matrix easily. The absorbed water in the matrix can exist as two different types: bound water and free water. Bound water is characterized by strong interactions with hydrophilic groups on the surface of the matrix and free water is present in capillaries and microvoids within the matrix (J. Zhou, *Polymer*, (1999)). From studies of hygrothermal effects of epoxy resin (L. Barral, *Journal of Thermal Analysis*, (1996),J. Zhou, *Polymer* (1999)), the bonding of water molecules with epoxy resin is divided into two types. Type I bonding corresponds to a water molecule that forms a single hydrogen bond within the epoxy resin network. This water molecule possesses lower activation energy and is easier to remove from the resin. Type II bonding is the result of a water molecule forming multiple hydrogen bonds within the resin network. This water molecule possesses higher activation energy and is correspondingly harder to remove. Type I bound water is the dominant form of the total amount sorbed water. Type I bound water acts as a plasticizer and decreases the glass transition temperature. In contrast, Type II bound water contributes to an increase of the glass transition temperature in water saturated epoxy resin by forming a secondary crosslinked network (L. Barral, *Journal of Thermal Analysis*, (1996),J. Zhou, *Polymer* (1999)). Results of this research are coincident with this model. Further research on examination of the different water molecule states in the cured matrix after water absorption is under investigation.

Biocomposite of the matrix and henequen fibers Biocomposites of the matrix blend and henequen fiber treated with different conditions were manufactured and the performances were investigated. Surface analysis and thermal stability of the henequen fibers were also investigated.

Figure 8A:
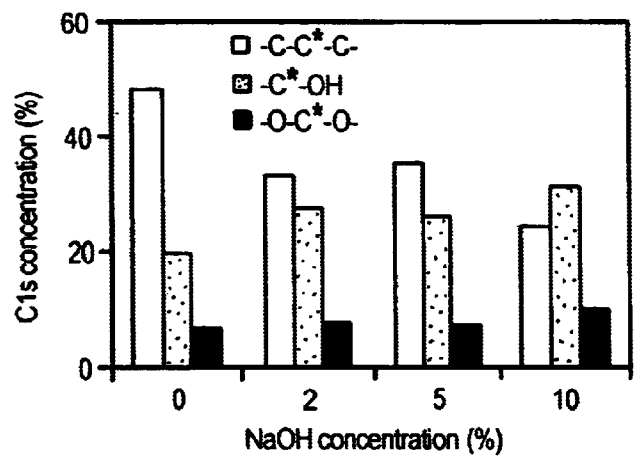
FIGS. 8A and 8B are graphs showing C1s and O1s concentrations with different NaOH concentrations.
Figure 8B:
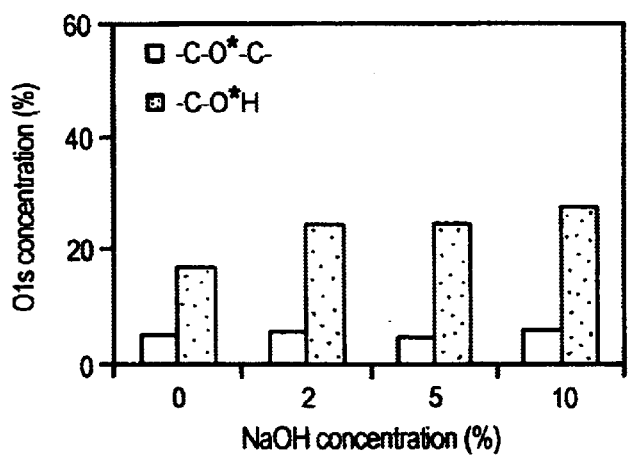

Surface Analysis of Henequen Fiber Surface analysis of raw and alkali treated fibers in different conditions are compared in Table 3. The atomic ratio of oxygen to carbon on the henequen fiber is generally increased and the nitrogen content is decreased after alkali treatment due to the removal of either impurities or protein from the fiber surface. FIGS. 8A and 8B show the changes of the carbon 1s and oxygen 1s spectra of henequen fibers after alkali treatment. The carbon 1s spectra was deconvoluted to three peaks that are assigned to —C—C*—C— (284.6 eV), —C*—O—H— (286.1 eV) and —O—C*—O— (287.6 eV). The oxygen curve is deconvoluted to two peaks that are assigned —O—C—O*— (530.0 eV) and —C—O*—H (532.0 eV). Generally, carbon 1s concentration due to —C—C*—C— is decreased and carbon 1s and oxygen is concentrations due to —C*—O*H are increased with increasing concentration of NaOH solution. Alkali treatment of henequen fibers increases the oxygen/carbon ratio and the hydroxyl groups on the fiber surface due to removal of impurities or to the formation of new hydroxyl groups. The decrease of the carbon 1s concentration from —C—C*—C— can be explained by the loss of lignin, which leads to the higher crystallinity of the fiber. This can lead to an increased in adhesion of the matrix to henequen fibers. The oxygen/carbon ratio, C 1s and O1s concentration do now show any difference between henequen fibers that are treated with 2 wt % and 5 wt % alkali solution. However the nitrogen concentration does change.

TABLE 3

Atomic Ratio of raw and Alkali treated Henequen Fibers (AT:alkali treated)

| Henequen | [C] % | [O] % | [O]/[C] | [N] % | [Ca] % |
|---|---|---|---|---|---|
| Raw | 74.1 | 22.6 | 0.31 | 2.9 | 0.4 |
| AT-2 wt % | 67.7 | 30.2 | 0.45 | 2.0 | 0 |
| AT-5 wt % | 68.4 | 29.7 | 0.43 | 1.5 | 0.4 |
| AT-10 wt % | 65.4 | 33.7 | 0.52 | 0.9 | 0 |

Figure 9:
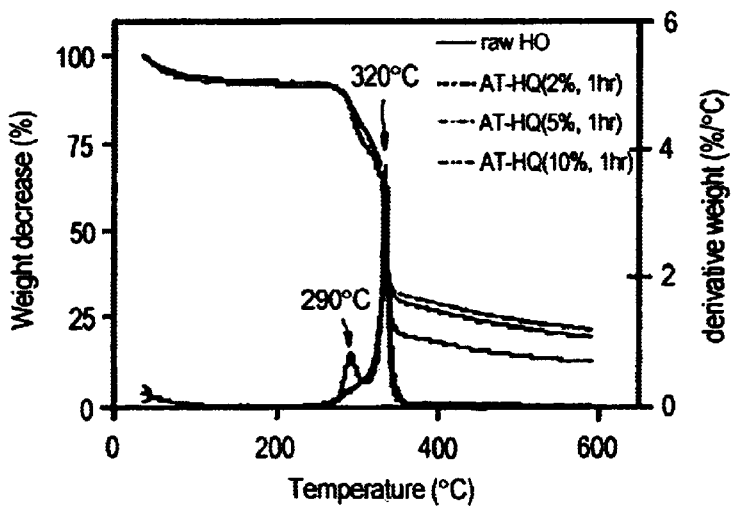
FIG. 9 is a graph of a TGA of raw and alkali treated henequens.

Thermal stability of Henequens Fibers treated with Solutions of Different NaOH Concentrations Henequen fibers are composed of approximately 60 wt % of cellulose, 28 wt % of hemicellulose, and 8 wt % of lignin. Hemicellulose has a very low thermal stability (A. K. Bledzki, *Prog. Polym. Sci*, (1999)) and can be easily removed from the fiber with an alkali treatment. FIG. 9 shows the thermal decomposition of raw and alkali treated henequen fibers. The decomposition peak of hemicellulose for the raw henequen fibers is shown around 290° C. This peak is not apparent on the TGA results of the alkali treated henequen fibers. A sharp drop in weight at 320° C., the onset of cellulose decomposition is apparent for all the samples. The plateau observed between 380° C. and 600° C. is attributed to oxidation and burning of the high molecular weight charred residues (A. V. Manuel, *J. Applied Polymer Science*, (1995)).

Figure 10A:
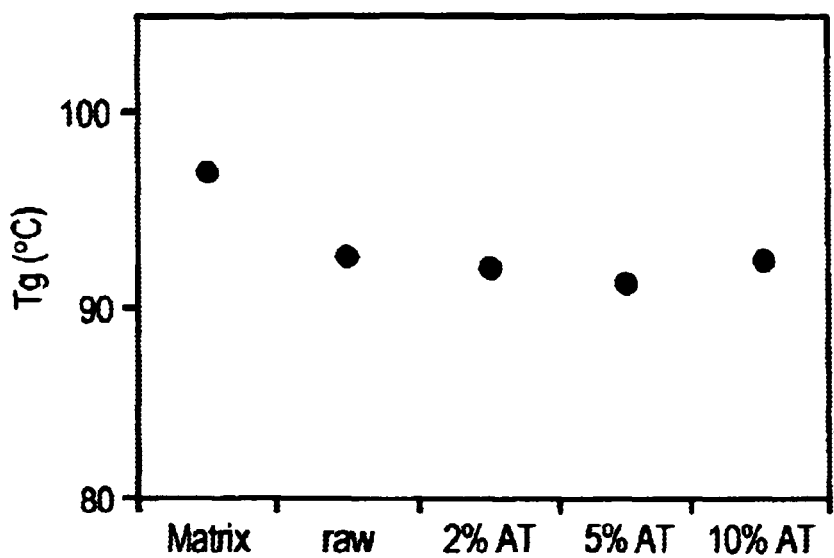
FIGS. 10A and 10B are graphs showing effects of raw and alkali treated fibers on the performances of biocomposite.
Figure 10B:
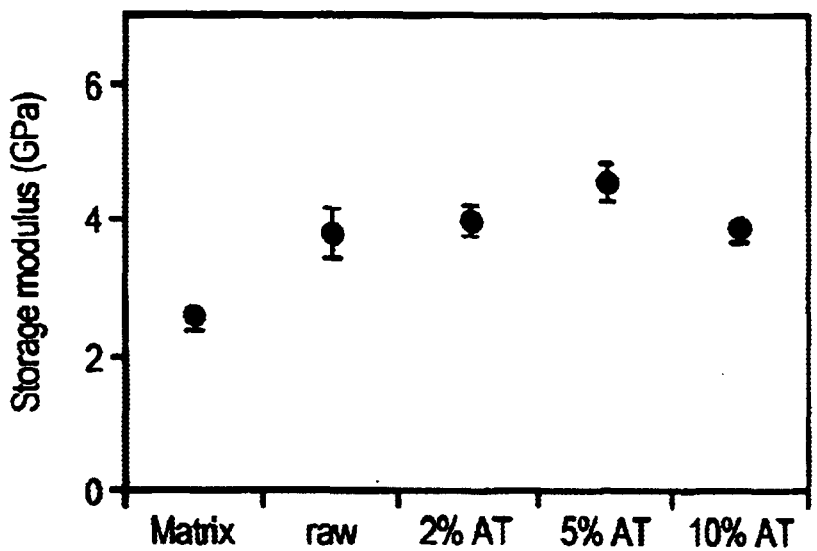

Thermo-Mechanical Performances of Biocomposites The effects of henequen fiber loading and alkali treatment on the thermo-mechanical performances of biocomposites are shown in FIGS. 10A and 10B. The storage modulus of biocomposite increased 147% when the raw henequen fibers are added to the matrix. Storage modulus of biocomposites made of alkali treated fibers increased up to 154%, 177% and 150% for fiber treatment with 2, 5, 10 wt % NaOH solutions, respectively. The superior mechanical properties of composites made with alkali treated henequen fibers may be attributed to the fact that alkali treatment improves the adhesive properties of the henequen surface by removing impurities and producing new hydroxyl groups on the surface of the fibers. In addition, the alkali treatment can lead to fiber fibrillation, breaking down of the fiber bundle into smaller fibrillar units. This increases the effective surface area available for contact with the matrix polymer (A. K. Mohanty, *SAMPE-ACCE-DOE-SPE*, (2000)). The storage modulus decrease when the fibers are treated in 10 wt % alkali solution can be explained by the comparative loss of crystallinity of henequen fibers due to the treatment with highly concentrated alkali solution.

An ecofriendly matrix of DGEBA and GMAEVC has been described in the Examples for biocomposites made with henequen fibers. The curing mechanism of DGEBA and GMAEVC is identified as etherification and esterification reactions of the hydroxyl and carboxylic functionalities of GMAEVC with the epoxy groups of the DGEBA resin. The cured matrix containing 50 wt % of GMAEVC exhibited thermal stability up to 300° C. The glass transition temperature and storage modulus of this cured matrix are as high as 97° C. and 2700 Pa, respectively. Weight increase and glass transition temperature decrease due to water uptake in the matrix were observed in a water absorption test. However, water absorption by the cured matrix did now produce any reduction in storage modulus. The decrease of glass transition temperature was recovered after heating this matrix at a temperature higher than 110° C. This matrix blend showed good compatibility with the henequen fibers and increased the mechanical properties when an alkali treated henequen fiber was used. This example shows the potential for development of cost effective and environmentally friendly biocomposites based on DGEBA and GMAEVC and natural fibers for automotive applications.

It is intended that the foregoing description be only illustrative of the present invention and that the present invention be limited only by the hereinafter appended claims.

We claim:

1. A curable polymer composition which comprises:
   (a) an epoxy resin precursor; and
   (b) a co-polymer produced by reaction of an alkyl polyglycoside, wherein alkyl is selected from the group consisting of alkyl containing 1 to 30 carbon atoms, and an organic anhydride which copolymer is a polyglycoside acid or acid ester, and optionally with a vinyl monomer, wherein the ration of (a) to (b) produces a cured polymer composition.

2. A curable polymer composition which comprises:
   (a) an epoxy resin precursor; and
   (b) a copolymer produced by reaction of an alkyl polyglycoside with an organic anhydride which copolymer is a polyglycoside acid or acid ester of the formula II or III as follows:

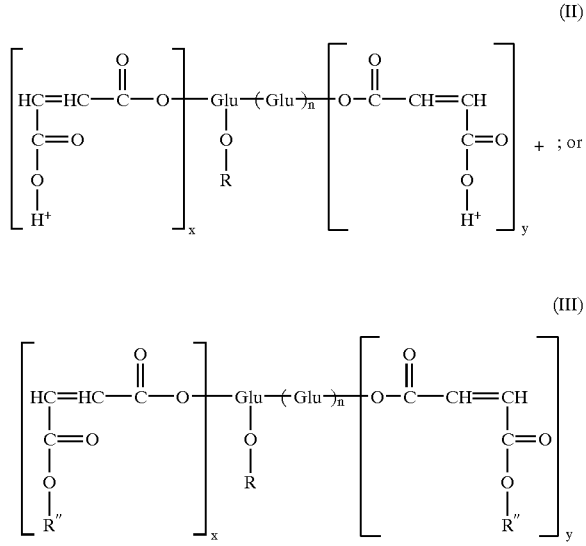

and mixtures thereof and optionally a vinyl monomer, wherein R and R" are alkyl containing 1 to 30 carbon atoms and wherein the ration of (a) to (b) produces a cured polymer composition, n is an integer between 0 and 10, x and y are integers between 0 and 4, but not x and y are 0 at the same time.

3. A curable polymer composition which comprises:
   (a) liquid epoxy resin; and
   (b) a copolymer produced by the reaction of an alkyl polyglycoside with an organic anhydride and a vinly monomer which compolymer has the formula as follows:

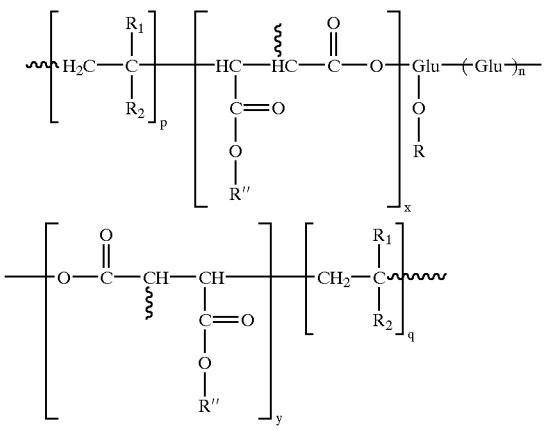

wherein Glu is a saccharide moiety which is derived from a sugar selected from the group consisting of α-D-glucose, fructose, mannose, galactose, talose, gulose, allose, altrose, idose, arabinose, xylose, lyxosc, ribose, and mixtures thereof, or by hydrolysis of a material selected from the group consisting of starch, corn syrups, maltodextrins, maltose, sucrose, lactose, maltotriose, xylobiose, mellibiose, cellobiose, raffinose, stachiose, levoglucosan, 1,6-anhydroglucofuranose, and mixtures thereof, and wherein the ratio of (a) to (b) produces a cured polymer composition, wherein $R_1$ and $R_2$ are substituent groups of the vinyl monomer or mixture of the vinyl monomers, wherein said vinyl monomer or mixture of vinyl monomers is selected from the group consisting of vinyl acetate, ethyl hexyl acrylate, butyl acrylate, ethyl acrylate, hydroxyethyl acrylate, hydroxyethyl methacrylate, lauryl acrylate, methyl methacrylate, methacrylic acid, acrylic acid, other acrylates, mixtures of different acrylate monomers, ethylene, 1,3-butadiene, styrene, vinyl chloride, vinylpyrrolidinone, other vinyl monomers, and mixtures thereof, R is selected from the group consisting of a C1 to C30 alkyl and mixtures thereof, R" is selected from the group consisting of a C1 to C30 alkyl and mixtures thereof, or a hydrogen, n is an integer ranging from 0 to 10; x and y are integers ranging from 0 to 4, but not x and y are 0 at the same time, p and q are integers ranging from 0 to 1000, but not both p and q are zero, and wherein ~~~ indicates continuing polymer chains.

4. The composition of claim 3 wherein Glu is an α-D-glucose moiety.

5. The composition of any one of claims 1, 2 or 3 wherein the molar ratio of (a) to (b) is about 1:1.

6. The composition of claim 2 wherein an alkyl polyglycoside is reacted with malic anhydride to form the polymer which is reacted with the vinyl monomer to form the copolymer.

7. The composition of claim 3 wherein $R^1$ and $R^2$ and R" are selected from the group consisting of hydrogen and n-butyl.

8. The composition of any one of claims 1, 2 or 3 including a filler.

9. The composition of any one of claims 1, 2 or 3 including fibers as a filler.

10. The composition of any one of claims 1, 2 or 3 containing cellulose fibers as a filler.

11. The composition of any one of claims 1, 2 or 3 containing an exfoliated clay or graphite as a filler.

12. The composition of any one of claims 1, 2 or 3 which is cured.

13. A process for forming a cured polymer composition which comprises:

(a) providing a mixture of (1) a liquid mixture of an epoxy resin precursor and (2) an alkyl polyglucoside-organic anhydride reaction product wherein alkyl is 1 to 30 carbon atoms which has optionally been polymerized with a vinyl monomer, wherein the ratio of (1) to (2) provides the cured polymer composition; and (b) heating the mixture to produce the cured polymer.

14. A process for forming a cured polymer composition which comprises:

(a) providing (1) a liquid epoxy resin precursor and (2) a liquid copolymer produced by reaction of alkyl polyglycoside and an organic anhydride which copolymer is an alkyl polyglycoside acid or acid ester of the formula II or III as follows:

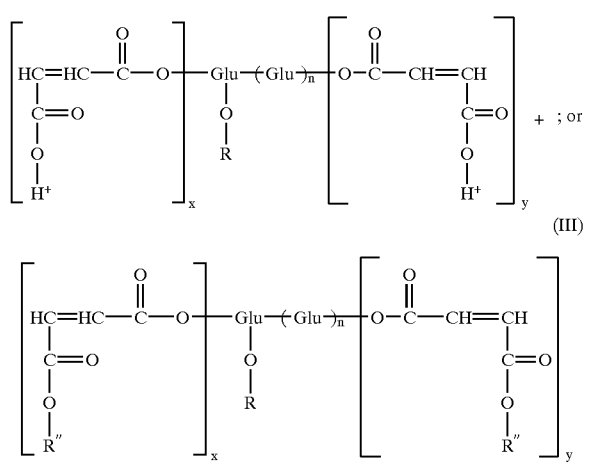

and mixtures thereof which has optionally been reacted with a vinyl monomer wherein R and R" are alkyl contain 1 to 30 carbon atoms, x and y are integers between 0 and 4 but not x and y are 0 at the same time and wherein the ratio of (1) to (2) produces the cured polymer composition; and (b) heating the mixture to produce the cured polymer composition.

15. A process for the preparation of a cured polymer composition which comprises:

(a) providing a mixture of
(1) a liquid epoxy resin; and
(2) a liquid copolymer produced by the reaction of an alkyl polyglycoside with an organic anhydride which copolymer has formula I as follows:

(I)

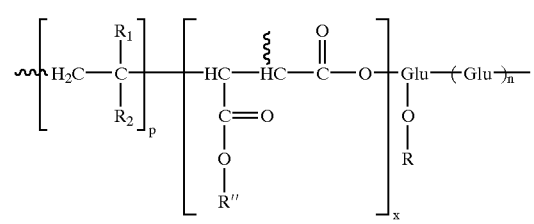

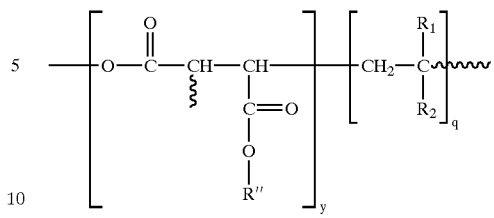

wherein Glu is a saccharide moiety which is derived from a sugar selected from the group consisting of α-D-glucose, fructose, mannose, galactose, talose, gulose, allose, altrose, idose, arabinose, xylose, lyxose, ribose, and mixtures thereof, or by hydrolysis of a material selected from the group consisting of starch, corn syrups, maltodextrins, maltose, sucrose, lactose, maltotriose, xylobiose, mellibiose, cellobiose, raffinose, stachiose, levoglucosan, 1,6-anhydroglucofuranose, and mixtures thereof, , wherein $R_1$ and $R_2$ are substituent groups of a vinyl monomer or mixture of vinyl monomers, wherein said vinyl monomer or mixture of vinyl monomers is selected from the group consisting of vinyl acetate, ethyl hexyl acrylate, butyl acrylate, ethyl acrylate, hydroxyethyl acrylate, hydroxyethyl methacrylate, lauryl acrylate, methyl methacrylate, methacrylic acid, acrylic acid, other acrylates, mixtures of different acrylate monomers, ethylene, 1,3-butadiene, styrene, vinyl chloride, vinylpyrrolidinone, other vinyl monomers, and mixtures thereof, R is selected from the group consisting of a C1 to C30 alkyl and mixtures thereof, R" is selected from the group consisting of a C1 to C30 alkyl and mixtures thereof, or a hydrogen, n is an integer ranging from 0 to 10; x and y are integers ranging from 0 to 4, but not x and y are 0 at the same time, p and q are integers ranging from 0 to 1000, but not both p and q are zero, and wherein ~~~ indicates continuing polymer chains, and wherein the ratio of (1) to (2) produces a cured polymer composition; and (b) heating the mixture to produce the cured polymer composition.

16. The process of claims 13, 14 or 15 wherein the molar ratio of (1) to (2) is about 1:1.

17. The process of any one of claims 13, 14 or 15 wherein the composition includes a filler.

18. The process of any one of claims 13, 14 or 15 including fibers as a filler.

19. The process of any one of claims 13, 14 or 15 containing cellulose fibers, an exfoliated clay or an exfoliated graphite as a filler.

20. The process of claim 14 wherein $R^1$, $R^2$ and R" are selected from the group consisting of hydrogen and n-butyl.

21. The composition of any one of claims 1, 2 or 3 wherein the epoxy resin precursor is derived from the diglycidyl ether of bisphenol A.

22. The process of claims 13, 14 or 15 wherein the epoxy resin precursor is derived from the diglycidyl ether of bisphenol A.

* * * * *

UNITED STATES PATENT AND TRADEMARK OFFICE
CERTIFICATE OF CORRECTION

PATENT NO. : 6,723,802 B2
DATED : April 20, 2004
INVENTOR(S) : Lawrence T. Drzal and Seong Ok Han Page 1 of 3

It is certified that error appears in the above-identified patent and that said Letters Patent is hereby corrected as shown below:

Column 2,
Line 27, formula III,

" 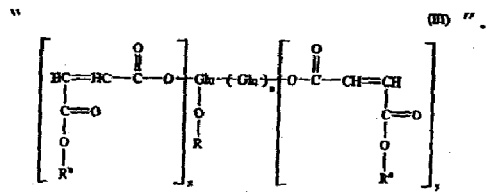 ".

should be

-- 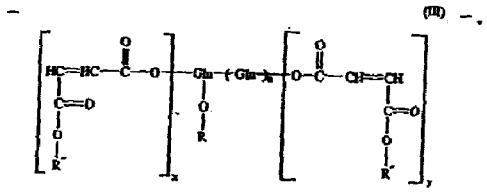 --.

Line 60, "lyxosc" should be -- lyxose --.

Column 3,
Line 40, "formula II or II as follows" should be -- formula II or III as follows --.
Line 58, formula III, " 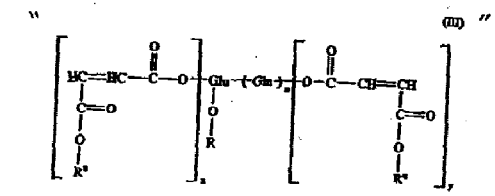 "

should be

-- 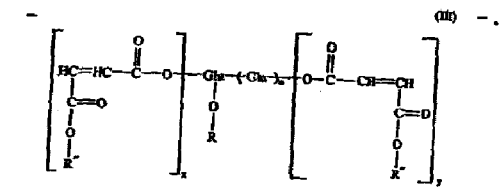 --.

Column 4,
Line 27, "sugar from the " should be -- sugar selected from the --.
Line 29, "lyxosc" should be -- lyxose --.

UNITED STATES PATENT AND TRADEMARK OFFICE
CERTIFICATE OF CORRECTION

PATENT NO. : 6,723,802 B2  
DATED : April 20, 2004  
INVENTOR(S) : Lawrence T. Drzal and Seong Ok Han It is certified that error appears in the above-identified patent and that said Letters Patent is hereby corrected as shown below:

Column 12,
Line 34, "is spectra" should be -- 1s spectra --.

Column 13,
Line 57, "oxygen is concentrations" should be -- oxygen 1s concentrations --.
Line 67, "do now show" should be -- do not show --.

Column 14,
Line 65, "did now produce" should be -- did not produce --.

Column 15,
Line 40, Formula II,

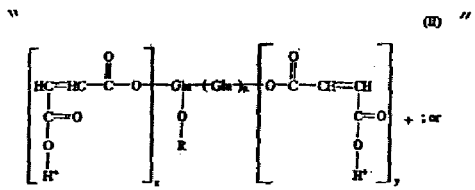

should be

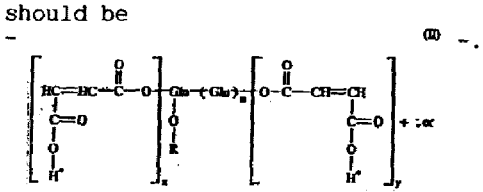

Column 16,
Line 24, "lyxosc" should be -- lyxose --.

Column 17,
Line 17, "formula II or II as follows" should be -- formula II or III as formula --.

UNITED STATES PATENT AND TRADEMARK OFFICE
CERTIFICATE OF CORRECTION

PATENT NO. : 6,723,802 B2
DATED : April 20, 2004
INVENTOR(S) : Lawrence T. Drzal and Seong Ok Han It is certified that error appears in the above-identified patent and that said Letters Patent is hereby corrected as shown below:

Column 17, cont'd.,
Line 25, formula II,

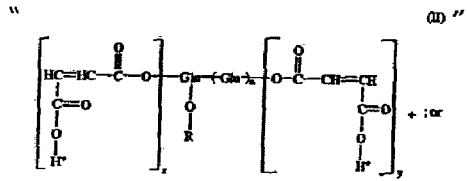

should be

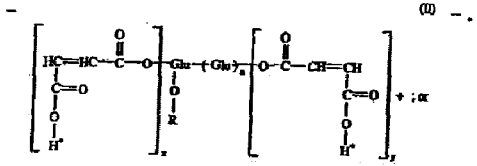

Column 18,
Line 16, "lyxosc" should be -- lyxose --.

Signed and Sealed this

Sixteenth Day of November, 2004

JON W. DUDAS
*Director of the United States Patent and Trademark Office*